United States Patent [19]

Verkaart

[11] Patent Number: 5,063,994
[45] Date of Patent: Nov. 12, 1991

[54] REFLUX FLUID HEATED PATIENT LINE

[75] Inventor: Wesley H. Verkaart, Duxbury, Mass.

[73] Assignee: Level 1 Technologies, Inc., Rockland, Mass.

[21] Appl. No.: 543,390

[22] Filed: Jun. 26, 1990

[51] Int. Cl.⁵ .............................................. F28D 7/10
[52] U.S. Cl. .................................... 165/154; 165/142
[58] Field of Search .......................... 165/154, 74, 142

[56] References Cited

U.S. PATENT DOCUMENTS

| | | | |
|---|---|---|---|
| 2,302,273 | 11/1942 | Sutton | 165/154 |
| 3,777,502 | 12/1973 | Michie, III et al. | 165/154 |
| 3,857,514 | 12/1974 | Clifton | 165/154 |
| 3,976,129 | 8/1976 | Silver | 165/154 |
| 4,714,108 | 12/1987 | Barry | 165/142 |
| 4,821,797 | 4/1989 | Allgauer et al. | 165/154 |
| 4,926,830 | 5/1990 | McNelley | 165/142 |

FOREIGN PATENT DOCUMENTS

| | | | |
|---|---|---|---|
| 624816 | 1/1934 | Fed. Rep. of Germany | 165/74 |
| 719974 | 3/1942 | Fed. Rep. of Germany | 165/154 |
| 559109 | 9/1923 | France | 165/154 |

*Primary Examiner*—John Rivell
*Assistant Examiner*—L. R. Leo
*Attorney, Agent, or Firm*—Dickinson, Wright, Moon, Van Dusen & Freeman

[57] ABSTRACT

A heat exchanger useful for supplying infusates over substantial distances uses an extrusion which provides a central tube for carrying an infusate and two outer channels for carrying a heat exchange fluid. A first of the channels carries the heat exchange fluid from an inlet end to an opposite end, and the other of the channels returns the heat exchange fluid to the inlet end. An end cap at the inlet end is easily connected to a source of heat exchange fluid and communicates with the channels. An end cap at the opposite end receives the heat exchange fluid from the first channel and redirects it to the second channel. Both of the end caps have connectors for facilitating connection with lines from a source of infusate and a patient.

17 Claims, 3 Drawing Sheets

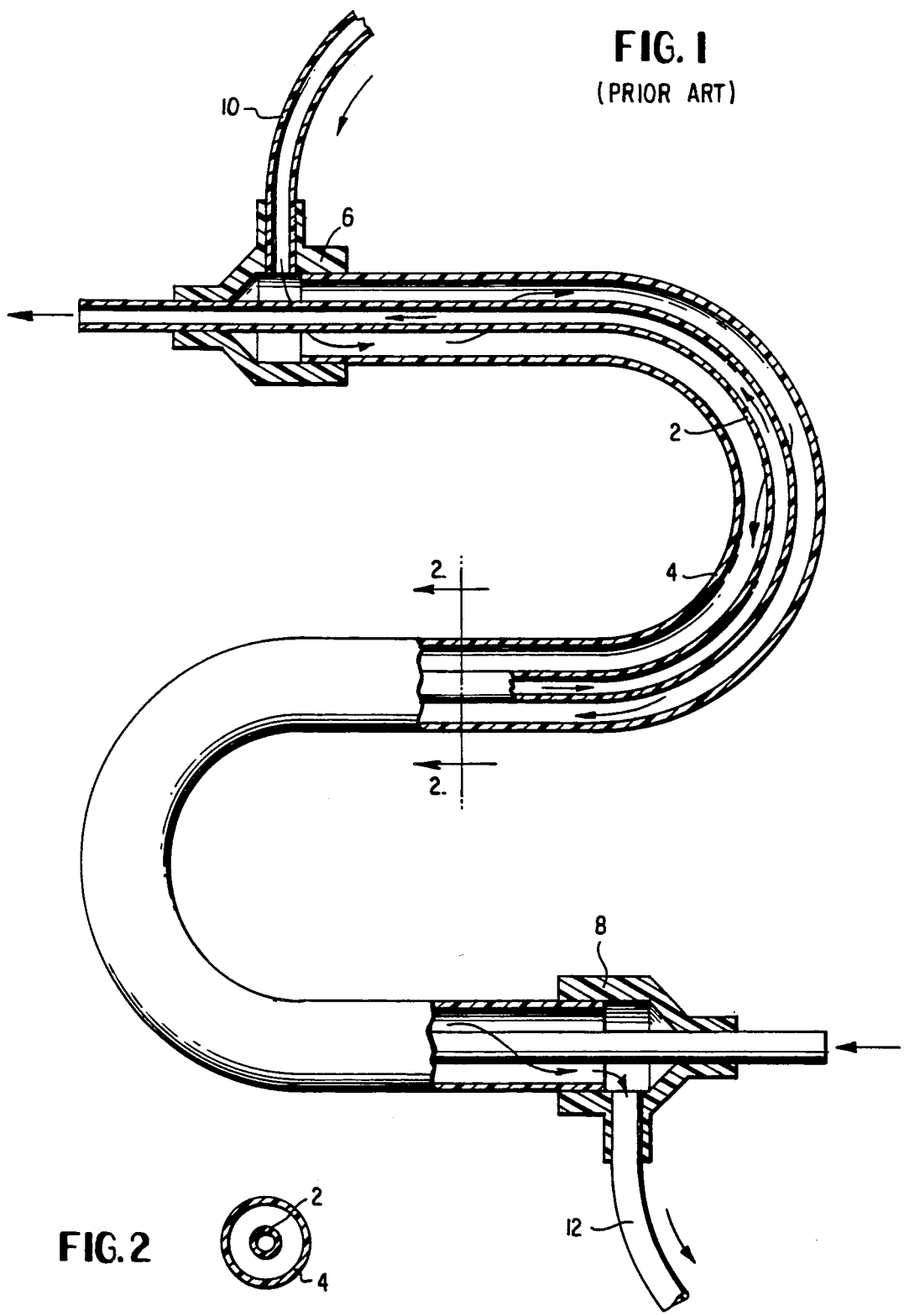

REFLUX FLUID HEATED PATIENT LINE

TECHNICAL FIELD

This invention relates to the art of heat exchangers. In particular the invention relates to disposable heat exchangers useful for changing or maintaining the temperature of physiological fluids.

BACKGROUND ART

It is known to use heat exchangers for warming a wide variety of fluids, including physiological fluids. U.S. Pat. No. 4,759,749 shows a heat exchanger in combination with a fluid supply system for circulating a warming fluid through a central tube of the heat exchanger. A physiological fluid is supplied to the space between the inner and outer tubes and is heated by contact with the warm inner tube.

A problem with fluid warming systems of this type arises when the flow rates are small, i.e., in the range of 100 ml/min. or less. At these rates, the physiological fluid leaving the heat exchanger cools in the delivery line between the heat exchanger and the patient. This problem worsens when the delivery line is of substantial length.

A heat exchanger having a central flexible tube and an outer flexible tube is known. The warming fluid is introduced at one end of the outer tube and flows out of an opening at the other end of the outer tube. This system is difficult to manufacture and presents several human engineering problems.

Heat exchangers having two concentric tubes formed by extrusion are also known. For example, U.S. Pat. No. 3,976,129 (Silver) shows an inner tube supported within an outer tube by fins, the structure being extruded from a metal, such as copper or aluminum.

SUMMARY OF THE INVENTION

In accordance with the invention, a heat exchanger is provided with means for connection to a source of physiological fluids (e.g., infusates) for carrying those fluids a substantial distance to the patient. The heat exchanger comprises an inner passage formed by an inner tube for carrying the infusate and two outer channels for carrying a heat exchange fluid in opposite directions. The outer channels are formed by dividing the space between the inner and outer tubes with a partition wall.

A first end cap at a first end of the heat exchanger redirects the heat exchange fluid which has flowed through a first of the channels into the second of the channels for return flow along the inner tube. A second end cap at a second end of the heat exchanger supplies the heat exchange fluid to the first channel and receives the returning heat exchange fluid from the second channel. Each of the end caps also has a connector in communication with the inner tube for facilitating connection of the inner tube to a supply of infusate at one end and to a patient at the other end.

The inner and outer tubes and the partitions are preferably formed by extrusion of a flexible polymer and may be easily made of any length. The end caps are of rigid or semi rigid plastic and can be attached to the ends of the inner and outer tubes in a simple manufacturing step. The materials are bio-compatible, and the product is preferably supplied in a sterile condition designed to be discarded after a single use.

The primary use of the apparatus of the invention is to heat physiological fluids which are stored at temperatures below normal body temperature. Accordingly, in the description which follows, the heat exchange fluid is a warming fluid. It should be noted, however, that the apparatus could as well be used to cool the infusate by using a cooling heat exchange fluid or to maintain the temperature by using a heat exchange fluid of appropriate temperature.

In addition, the device of the invention may be used outside the medical field, e.g., in a chemical laboratory, for a solar hot water system, or in industrial food preparation, and may be used in medical applications unrelated to infusates, e.g., enteral feeding and donor organ perfusion.

BRIEF DESCRIPTION OF THE DRAWINGS

FIG. 1 is a side view in partial cross section of a known heat exchanger.

FIG. 2 is a cross section along line 2—2 of FIG. 1.

DETAILED DESCRIPTION OF THE DRAWINGS

Figure 3:
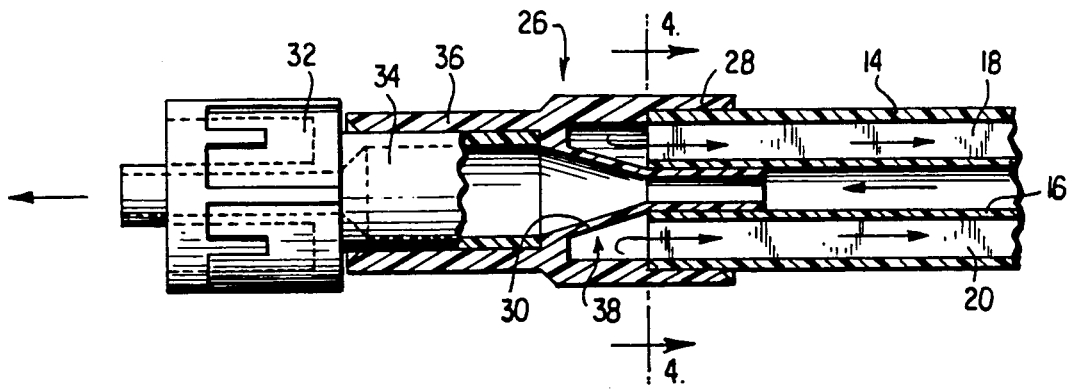
FIG. 3 is a side view in partial cross section of a first end of a heat exchanger in accordance with the invention.

FIG. 1 illustrates a known heat exchanger used with physiological fluids. An inner flexible plastic tube 2 is concentric with an outer flexible plastic tube 4. A first end cap 6 allows a warming fluid to be introduced into the space between the inner and outer tubes, while a second end cap 8 allows the warming fluid to be withdrawn. A first warming fluid supply tube 10 is connected to the end cap 6, and a second warming fluid supply tube 12 is connected to end cap 8. A first end of the inner tube 2 is supplied with a physiological fluid, or infusate, to be heated, and the warmed fluid exits the opposite end.

The exchanger shown in FIGS. 1 and 2 is difficult to manufacture and further presents the problem that the warming fluid supply tubes 10 and 12 must be connected to opposed ends of the outer tube 4. This presents a significant human engineering problem because these tubes may have to be rather lengthy and can become entangled in other equipment in the hospital room.

A preferred embodiment of the invention which solves these problems is shown in FIGS. 3 through 8. An outer tube 14 surrounds and is preferably concentric with an inner tube 16. The space between the inner and outer tube is designed to carry a warming fluid, and the inner tube is designed to carry an infusate to be warmed. The inner and outer tubes are connected by a first partition wall 18 which extends between one side of the inner tube and the outer tube and by a second partition wall 20 which extends between the other side of the inner tube and the outer tube. These partition walls divide the interior of the outer tube into two channels as shown more clearly in FIGS. 4, 5, and 7.

Figure 4:
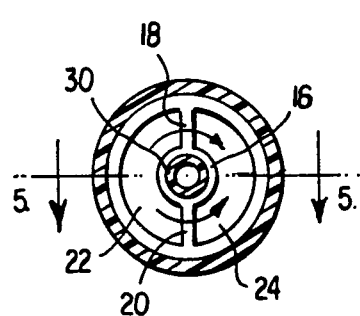
FIG. 4 is a cross section along line 4—4 of FIG. 3.
Figure 5:
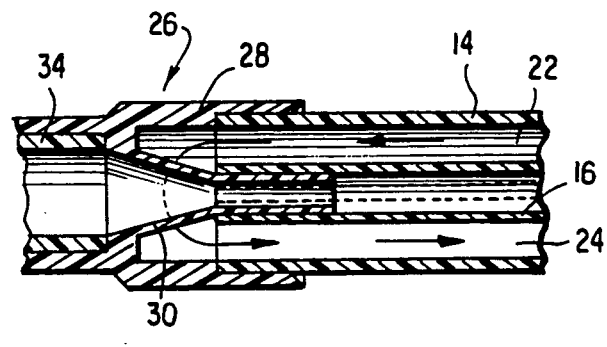
FIG. 5 is a cross section along line 5—5 of FIG. 4.
Figure 6:
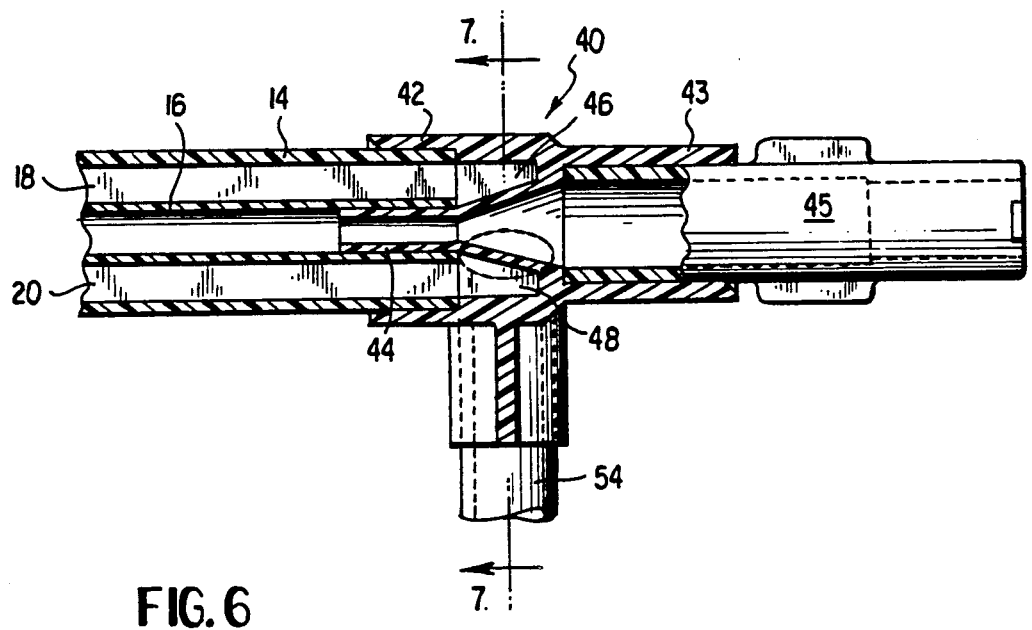
FIG. 6 is a side view in partial cross section of a second end of a heat exchanger in accordance with the invention.
Figure 7:
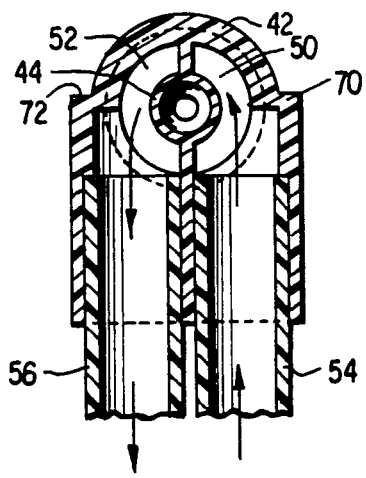
FIG. 7 is a cross section along line 7—7 of FIG. 6.

A first channel 22 carries fluid from the second end shown in FIGS. 6 and 7 to the first end shown in FIGS. 3-5. The second channel 24 carries the warming fluid back to the second end for return to the source of warming fluid. The fluid in channel 22 is redirected by the end cap 26 which is secured to the ends of the inner and outer tubes.

The inner and outer tubes and the partition walls are preferably integral and are manufactured by extrusion of a flexible bio-compatible polymer. The extrusion can be cut to any desired length to facilitate manufacture of a variety of products to meet various needs.

End cap 26 comprises two cylindrical portions and a conduit. A first cylindrical portion 28 engages the outer surface of outer tube 14 and may be sealingly secured thereto, e.g. by cement. A conduit 30 is incorporated into a bottom wall of the first cylindrical portion and tapers from a larger diameter to a smaller diameter which is received in the inner tube 16 and may be sealingly secured thereto. A male luer fitting 32, for attachment to a line leading to the patient, includes a stub 34 which is received in a second cylindrical portion 36 of the end cap 26. Male luer 32 is thus placed in fluid communication with the conduit 30. The space between the conduit 30 and the inner surface of the outer portion 28 forms chamber 38 for receiving the warming fluid and reversing its direction as it emerges from channel 22 and enters channel 24.

Infusate in the inner tube 16 communicates with the luer by way of the conduit 30.

Referring now to FIGS. 6 and 7, a second end cap 40 is similar to end cap 26 and includes a first cylindrical portion 42 which engages the outer surface of outer tube 14. An inner conduit 44 is incorporated into the bottom wall of the cylindrical portion 42 and tapers from a larger diameter to a smaller diameter capable of being received in inner tube 16, as described with respect to end cap 26. A female luer 45 is received in a second cylindrical portion 43 such that the female luer is in fluid communication with conduit 44. End cap 40 differs from end cap 26, however, in that it includes partition walls 46 and 48 which are aligned, respectively, with walls 18 and 20 when the cap 40 is attached to the extrusion forming the inner and outer tubes as shown in the drawing figures.

FIG. 7 illustrates more clearly how the partition walls divide the space between the conduit 44 and the first cylindrical portion 42 of end cap 40 into an inlet chamber 50 and an outlet chamber 52 which align, respectively, with channels 22 and 24. An inlet conduit 54, shown as a cylindrical protrusion, is incorporated into the wall forming inlet chamber 50 to supply a warming fluid to inlet chamber 50, and a similar outlet conduit 56 is incorporated into the wall forming outlet chamber 52 to return the warming fluid to the source of fluid.

While the inlet and outlet conduits 54 and 56 are preferably smooth cylindrical nipples integral with the walls of the chambers, other arrangements are possible, such as tapped holes, or threaded or barbed nipples.

It will be appreciated that the fluid flows into the inlet duct 54 from a source of warming fluid, flows through first channel 22, is directed by end cap 26 to flow through second channel 24, and returns to the source of fluid through outlet conduit 56 by way of outlet chamber 52.

The end caps are preferably made of rigid or semirigid bio-compatible plastic and are preferably bonded to the extrusion by an appropriate solvent or adhesive as known in the art.

Figure 8:
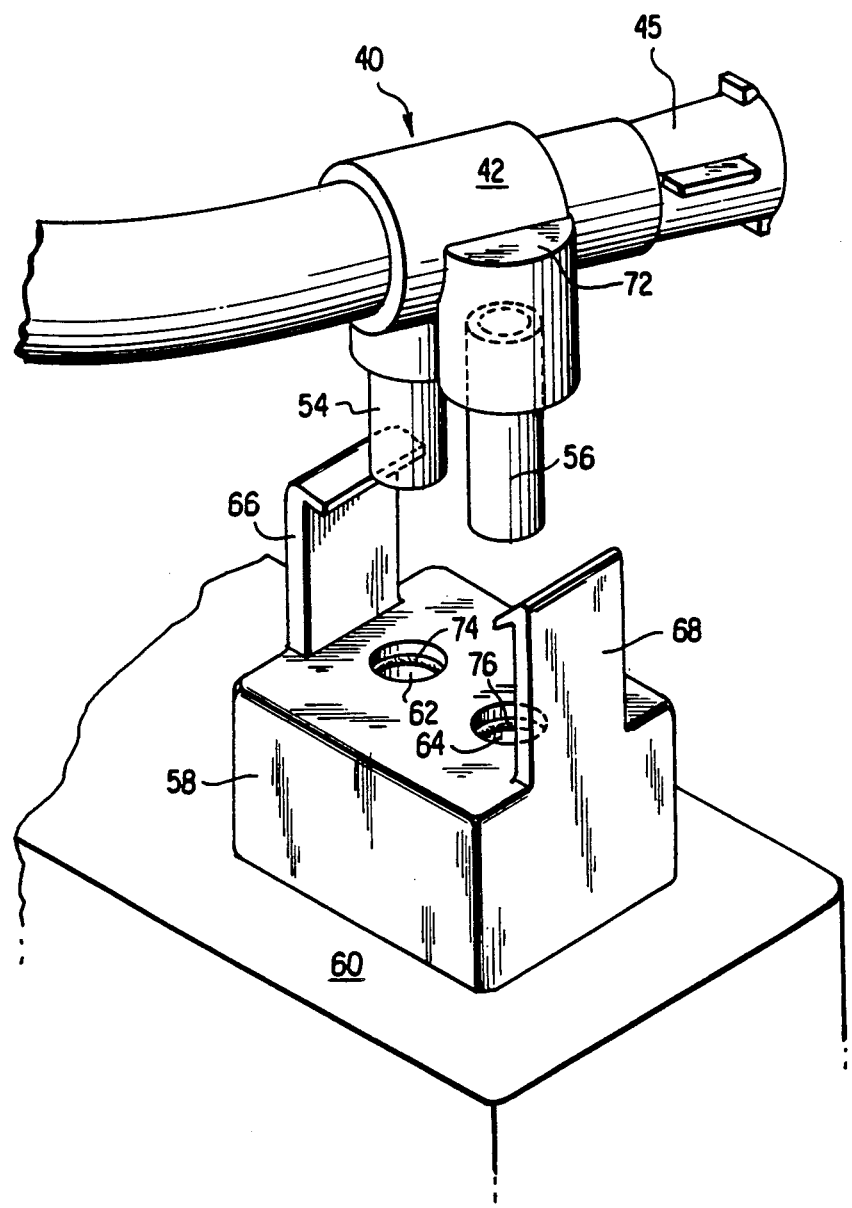
FIG. 8 is a perspective of the second end showing a connection to a supply of heat exchange fluid.

FIG. 8 illustrates a connection between the end cap 40 and a source of warming fluid. A connector 58 is mounted to a housing 60 which contains a source of warming fluid. Connector 58 includes cylindrical openings 62 and 64 which are adapted to receive respective ones of nipples 54 and 56. Opening 62 is connected to an outlet of a source of warming fluid, while opening 64 is connected to a return line for the warming fluid. The system for supply of warming fluid may be that shown in my U.S. Pat. No. 4,759,749 or a similar apparatus.

Clips 66 and 68 engage shoulders 70 and 72 when the end cap 40 is in such a position that the nipples are fully engaged with the openings to allow the circulation of fluid through the heat exchanger.

Preferably, the openings 62 and 64 include O-ring seals 74 and 76 for allowing the nipples to be quickly and easily inserted into the openings while still providing good fluid sealing.

Modifications within the scope of the appended claims will be apparent to those of skill in the art.

I claim:

1. A heat exchanger comprising a first tube carrying a first fluid, a second tube spaced from and surrounding said first tube for carrying a second fluid, partition means for dividing the space between said first and second tubes into first and second channels for carrying said second fluid, and first end cap means adjacent a first end of said first tube and a first end of said second tube for receiving said second fluid which has flowed through said first channel and for redirecting said second fluid to flow into said second channel, wherein said partition means terminates substantially flush with said first end of said first tube and said first tube and said first end cap means are separate elements.

2. A heat exchanger according to claim 1 further comprising second end cap means adjacent a second end of said first tube and a second end of said second tube for supplying said second fluid to said first channel and for receiving said second fluid from said second channel.

3. A heat exchanger according to claim 2 wherein each of said first and second end cap means includes means for fluid communication with said first tube.

4. A heat exchanger according to claim 3 wherein said first and second tubes and said partition means are integral.

5. A heat exchanger according to claim 4 wherein said first and second tubes and said partition means are an extrusion.

6. A heat exchanger according to claim 2 wherein said second end cap means comprises conduit means for fluid communication with said inner tube, means for engaging said second tube, inlet means for communicating with said first channel and outlet means for communicating with said second channel.

7. A heat exchanger according to claim 6 wherein said conduit means of said second end cap means and said means for engaging form a chamber and said second end cap further comprises wall means for aligning with said partition means and for dividing said chamber into inlet and outlet chambers.

8. A heat exchanger according to claim 7 wherein said inlet means comprises a cylindrical protuberance communicating with said inlet chamber and said outlet means comprises a cylindrical protuberance communicating with said outlet chamber.

9. A heat exchanger according to claim 8 further comprising fluid supply means for supplying a heat exchange fluid to said inlet means and for receiving said heat exchange fluid from said outlet means.

10. A heat exchanger according to claim 9 further comprising an inlet receptacle for receiving said first cylindrical protuberance and an outlet receptacle for receiving said second cylindrical protuberance and means for securing said second end cap means to said heat exchange fluid supply means.

11. A heat exchanger according to claim 10 wherein each of said inlet and outlet receptacles comprises a cylinder and a seal on the interior thereof for slidingly receiving a respective one of said inlet and outlet cylindrical protuberances.

12. A heat exchanger according to claim 6 wherein said first end cap means comprises conduit means for fluid communication with said first tube and means for engaging said second tube.

13. A heat exchanger according to claim 12 wherein said first and second tubes and said partition means are an integral extrusion of flexible bio-compatible plastic, said first and second end caps are made of at least semi-rigid plastic, and said first and second end caps are bonded to said extrusion.

14. A heat exchanger according to claim 12 wherein said conduit means and said means for engaging form a chamber for receiving said second fluid from said first channel and for redirecting said second fluid to flow into said second channel.

15. A heat exchanger according to claim 2 wherein a second end of said partition means terminates substantially flush with said second end of said first tube and said first tube and said second end cap means are separate elements.

16. A heat exchanger comprising a first tube for carrying a first fluid, a second tube spaced from and surrounding said first tube for carrying a second fluid, partition means for dividing the space between said first and second tubes into first and second channels for carrying said second fluid, wherein said first tube, said second tube, and said partition means are of substantially equal lengths, and further comprising first end cap means separate from said first and second tubes and adjacent first ends of said first and second tubes for receiving said second fluid which has flowed through said first channel and for redirecting said second fluid to flow into said second channel.

17. A heat exchanger comprising a first tube for carrying a first fluid, a second tube spaced from and surrounding said first tube for carrying a second fluid, partition means having a length substantially that of said first tube for dividing the space between said first and second tubes into first and second channels for carrying said second fluid, and first end cap means separate from said first tube adjacent first ends of said first and second tubes for receiving said second fluid which has flowed through said first channel and for redirecting said second fluid to flow into said second channel.

* * * * *